(12) United States Patent
Arkles et al.

(10) Patent No.: US 7,265,236 B2
(45) Date of Patent: Sep. 4, 2007

(54) POLYPODAL SILANES WITH EMBEDDED HYDROPHILICITY

(75) Inventors: Barry C. Arkles, Dresher, PA (US); Youlin Pan, Langhorne, PA (US)

(73) Assignee: Gelest, Inc., Morrisville, PA (US)

( * ) Notice: Subject to any disclaimer, the term of this patent is extended or adjusted under 35 U.S.C. 154(b) by 192 days.

(21) Appl. No.: 11/063,069

(22) Filed: Feb. 22, 2005

(65) Prior Publication Data

US 2005/0187400 A1    Aug. 25, 2005

Related U.S. Application Data

(60) Provisional application No. 60/546,729, filed on Feb. 23, 2004.

(51) Int. Cl.
*C07F 7/04* (2006.01)
(52) U.S. Cl. .................................... 556/482
(58) Field of Classification Search ................. 556/482
See application file for complete search history.

(56) References Cited

U.S. PATENT DOCUMENTS 4,526,996 A * 7/1985 Kilgour et al. ............ 556/413

6,743,882 B2 * 6/2004 McGall et al. ............... 528/10

OTHER PUBLICATIONS

Shende et al., Sol-Gel Poly(ethylene glycol) Stationary Phase for High-Resolution Capillary Gas Chromatography, Anal. Chem.; (Article); 2003; 75(14); 3518-3530.*

* cited by examiner

*Primary Examiner*—Johann Richter
*Assistant Examiner*—Chukwuma Nwaonicha
(74) *Attorney, Agent, or Firm*—Akin Gump Strauss Hauer & Feld LLP

(57) ABSTRACT

A polypodal silane compounds are provided for use as a bonded phase and which have embedded hydrophilicity. The compounds have at least two podal branches bonded via an ether linkage or alkoxy group to a hydrophilic group. Each podal branch has a silicon atom which is bonded to each podal branch through a Si—C bond and each of the podal branches is capable of bonding to a siliceous substrate through at least one hydrolyzable functional group capable of being displaced by a Si—O bond. Bonded phases using such compounds and substrates having such compounds bonded to their surface are also described, as well as a method for preparing a bonded phase.

11 Claims, No Drawings

POLYPODAL SILANES WITH EMBEDDED HYDROPHILICITY

CROSS-REFERENCE TO RELATED APPLICATIONS

This application claims the benefit of U.S. provisional patent application No. 60/546,729, filed on Feb. 23, 2004, the entire disclosure of which is incorporated herein by reference.

BACKGROUND OF THE INVENTION

Liquid phase chromatography and extraction techniques are dependent on the interaction of a region bonded to a solid support and a solvent environment containing the solutes of interest. The support is stationary with respect to the liquid or solvent phase. The interacting region is designated as a "bonded-phase" or "interphase." An overview of this technology is provided by C. Horvath in Silylated Surfaces ed. D. Leyden, Gordon & Breach 1980 p. 269, the contents of which are incorporated herein by reference. Features which make a bonded phase desirable are reproducible non-bonding interactions with solutes in the mobile phase under a variety of operating conditions including temperature, pressure, and nature of solvent and the stability over a period of time.

The most widely used bonded phases are hydrophobic phases derived from octadecyl functional silanes. Specifically, octadecyldimethylchlorosilane and octadecyltrichlorosilane treated silicas are most widely used in high pressure liquid chromatography and solid-phase extraction, respectively.

Hydrophobic phases frequently must be "conditioned" with an organic solvent prior to applying analytical samples in dissolved aqueous or mixed solvent water mixtures or utilizing aqueous or mixed solvent water mixtures as mobile phases in order to achieve acceptable results. One approach to eliminating the need for conditioning is to apply a silane which contains a polar group in relatively close proximity to the point of attachment of the silane to the inorganic substrate. This approach is sometimes referred to as buried or embedded hydrophilicity. In general, these phases suffer from column bleed, i.e., the slow loss of the bonded phase observed either directly in changes in elution base-line or indirectly by loss in efficacy of separation. The introduction of polar groups close to the attachment of the silane to the substrate, while solving the problem of conditioning, brings water molecules to the substrate surface where they can effect a hydrolysis of Si—O—Si bonds. The problem is particularly exacerbated in the most common phases with embedded hydrophilicity that contain polar protic groups such as amides or urethanes. Similar issues occur in DNA and protein array technology in which substitutents on the bonded phase are more complex structures associated with peptides or oligonucleotides. The technologies often utilize immobilization technology and carry out analysis at greater pH ranges particularly at pH>7.0 where the scission of Si—O—Si is accelerated. Dipodal silanes with buried amines are discussed by McGall and Forman, U.S. Pat. No. 6,743,882, however these materials do not possess optimum stability because the diamine structure can be particularly active in dissolution of silicon dioxide surfaces.

Thus, there is a need in the art to provide bonded phases with embedded hydrophilicity which provide stable bonds with the a substrate and which allow for interaction of solutes with the hydrophobic bonded portion in a water and/or solvent environment with minimal negative effects in the form of bed collapse, diffusion or detachment of the bonded phase.

SUMMARY OF THE INVENTION

The invention includes a polypodal silane compound for use as a bonded phase and having hydrophilicity, comprising at least two podal branches bonded via an ether linkage or alkoxy group to a hydrophilic group, wherein each podal branch has a silicon atom, the silicon atoms are bonded to each podal branch through a Si—C bond and each of the podal branches is capable of bonding to a siliceous substrate through at least one hydrolyzable functional group capable of being displaced by a Si—O bond.

Also included within the invention is a polypodal silane compound comprising a structure according to Formula (I):

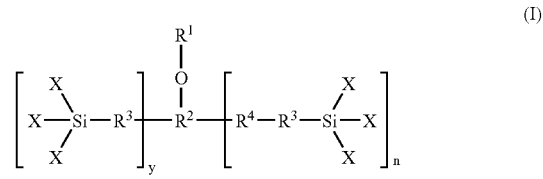

wherein:
$R^1$ is selected from hydrogen, and substituted and unsubstituted, branched and straight chain, alkyl, alkenyl, alkynyl, aryl, alkylene ether, alkenyl ether, alkynyl ether or aryl ether groups, and wherein, in $R^1$, oxygen atoms are not bonded together so as to form peroxy functionality;
$R^2$ is selected from substituted and unsubstituted, branched and straight chain alkyl and alkylene ether groups;
$R^3$ is selected from substituted and unsubstituted, branched and straight chain alkyl groups, wherein each $R^3$ group in Formula (I) may be the same or different;
$R^4$ is selected from substituted and unsubstituted, branched and straight chain alkyl, alkylene, alkylene ether and alkenyl ether groups, and an ether linkage;
X is a hydrolyzable group capable of bonding to a siliceous substrate and of being displaced by a silicon-oxygen bond or a non-hydrolyzable organic functional group, wherein at least one of the X groups on each Si atom is hydrolyzable;
n is 0 or an integer which is no greater than 3;
y is 0 or an integer which is no greater than 3; and
wherein $2 \leq n+y \leq 3$; and n and y are never both zero.

A method for preparing a bonded phase is provided herein which comprises reacting a polypodal silane compound with chromatographic silica to form a bonded phase for separation, wherein the polypodal silane comprises at least two podal branches bonded by an ether linkage or alkoxy group to a hydrophilic group, wherein each podal branch has a silicon atom, the silicon atoms are bonded to each podal branch through a Si—C bond and each of the podal branches is capable of bonding to a siliceous substrate through at least one hydrolyzable functional group capable of being displaced by a Si—O bond.

The invention further includes a siliceous substrate bonded to a polypodal silane compound, wherein the polypodal silane compound has at least two podal branches bonded by an ether linkage or alkoxy group to a hydrophilic group, wherein each podal branch has a silicon atom, the silicon atoms are bonded to each podal branch through a Si—C bond and each of the podal branches forms at least one Si—O—Si bond with the substrate.

DETAILED DESCRIPTION OF THE INVENTION

A polypodal silane compound is described herein which has two or more silicon atoms each of which is bonded to at least one hydrolyzable functional group capable of bonding to a substrate, preferably a substrate comprising silicon, referred to herein as a "siliceous substrate," and which has a polar substituent as a hydrophilic region capable of hydrogen-bonding with water. These silicon compounds can be used as bonded phases having embedded hydrophilic groups (including hydroxyl) which possess excellent hydrolytic stability in comparison with compounds currently used in similar applications, such as liquid chromatography and extraction techniques. Methods of bonding these compounds to a substrate comprising silicon to form a bonded phase are also described. Exemplary methods of preparing the compounds are also described.

The compounds described herein have advantageous effects which minimize negative effects of Si—O—Si bonds within the structure by including two or more silicon atoms that are neither bound to one another nor bound to the remaining structure through an Si—O—Si siloxane bridge, and yet are independently capable of bonding through Si—O—Si bonds with siliceous substrates.

The structures include a bonded region in the form of two or more branches which are connected through at least one ether linkage to a hydrophilic region. When there are two silicon atoms capable of bonding with the substrate and two such branches, the compounds are referred to herein as "dipodal" from the Greek meaning "two feet;" when there are two or more silicon atoms and branches, the compounds are referred to herein as "polypodal." The compounds within the scope of the invention herein include polypodal compounds, preferably dipodal compounds.

The polypodal silane compounds may be used as a bonded phase with embedded hydrophilicity, however, they may have other uses as well. The compounds have at least two podal branches bonded to a hydrophilic group via an ether linkage or alkoxy group, which may be an alkyl or alkoxy group that terminates in an ether. As used herein, "alkoxy" encompasses any carbon-based chain group of one or more carbon atoms and having one or more oxygen atoms which are bonded to and/or incorporated into the carbon chain in the form of an ether linkage, C—O—C.

Each podal branch within the compound has at least one silicon atom. The silicon atoms are located towards the bonding end of the compound and are bonded to each podal branch through a Si—C bond (instead of an Si—O—Si link as in prior compounds) and each of the podal branches is capable of bonding to a siliceous substrate through at least one hydrolyzable group bonded to the the silicon which is hydrolyzable group is capable of being displaced by a Si—O bond. Preferably, each silicon has three of such groups.

Preferably, the compounds of the invention may be represented by the general chemical structure shown in Formula below (I):

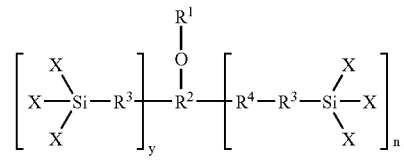

$R^1$ in the above formula may a hydrogen atom or another organic functional group in the form of a substituted or unsubstituted, branched or straight chain carbon based groups such as an alkyl, alkenyl, alkynyl, aryl, alkylene ether, alkenyl ether, alkynyl ether and aryl ether, however, in the various ether groups, it is preferred that oxygen bonds are not bonded to one another directly so as to form peroxy functionality in $R^1$. $R^1$ can be of shorter or longer chain lengths and should be capable of interacting, binding or forming covalent linkages with complex organic groups such as biological polymeric materials including peptides, polypeptides, oligonucleotides, or proteins which bonded to the oxygen in Formula (I) by an ester or amide linkage.

In Formula (I), the branched or "podal" groups (which could be in the form of either of the groups shown in the right and left brackets in formula (1)), branch from $R^2$. $R^2$ may be a substituted or unsubstituted, branched or straight chain alkyl or alkylene ether group.

$R^3$ functions to attach the Si—$X_3$ group to the podal branch and according to the preferred embodiment herein includes no oxygen atoms such that a C—Si bond is formed and interference with the bonded phase is minimized. Thus $R^3$ is preferably a substituted or unsubstituted, branched or straight chain, alkyl group, and each $R^3$ group in Formula (I) may be the same or different from one another.

In formula (I), when at least one branch has a configuration in the manner of the right-hand branch shown above, $R^4$ functions to provide enhanced ether linkages or other oxygen or hydrophilic functionality toward the hydrophilic region of the compound and may be a substituted or unsubstituted, branched or straight chain alkyl, alkylene ether, alkene or alkenyl ether groups or simply be a single ether linkage.

At least one X group on each silicon atom is a hydrolyzable group capable of bonding to a siliceous substrate and capable of being displaced by a silicon-oxygen bond. However, X groups may also encompass non-hydrolyzable organic functional groups. Exemplary X groups include but are not limited to alkoxy groups, halogens, carboxylates, or simple non-hydrolyzable organic functional groups. However, at least one of the X groups on each silicon atom must be a hydrolyzable group. It is preferred that all of the X groups are hydrolyzable groups. The hydrolyzable groups may be the same or different from each of the other X groups. Preferred alkoxy groups are methoxy and ethoxy. Preferred halogens include bromine and chlorine, most preferably chlorine. Preferred carboxylates include but are not limited to acetate. The preferred simple non-hydrolyzable organic functional groups include but are not limited to methyl, ethyl and isopropyl.

In Formula (I), depending on the number and configuration of the podal branches, n can be 0 or an integer which is no greater than 3; and y is 0 or an integer which is no greater than 3. It is also preferred that 2≦n+y≦3; and that n and y are never both zero.

As used herein, "substituted" groups include known substituent groups which may attach to any of the organic groups described herein that would benefit or promote the particular use of the resulting compound in its desired application, for example as a bonded phase. Exemplary substitution groups include reactive functional groups and non-reactive groups, including halogens, sulfur- or phosphorus-containing groups, carboxyl, hydroxyl, amide, amine, imine, and whole or partial ring structures. However, care must be taken that groups are selected so as to not affect the functioning of a hydrophobic of hydrophilic region of the polypodal compounds.

The hydrophilicity of the polypodal compounds can be modified and increased by introducing multiple ether linkages in the hydrophilic group $R^1$, or by providing additional ether links nearer to the hydrophilic portion in $R^2$ and/or $R^4$. Preferred structures useful in the present invention are set forth below as Formulae (II) and (III). It is preferred that in Formula (I), $R^1$ is from 1 to about 30 carbon atoms, preferably 1 to 20 carbon atoms in length. It is preferred that $R^2$, $R^3$ and $R^4$ are from 1 to 10 carbon atoms, and are preferably 3 to 5 carbon atoms and that in the Formulae below, r, s, t, q and v are from 1 to 10 carbon atoms and preferably 3 to 5 carbon atoms. Chain length and group size should be determined in part based on the desired end effects to be achieved through use of the polypodal silane compounds of the invention as described herein.

In another preferred embodiment, according to formula (I), n is 2 and y is 0. Further, $R^2$ is methyl and $R^3$ is an unsubstituted, straight chain alkyl group. $R^4$ is an unsubstituted, straight chain, alkoxy having at least one ether linkage which is terminal and that bonds $R^4$ to $R^3$. X is preferably selected from the group consisting of methyl, ethoxy, chlorine, acetate, methyl and isopropyl. This embodiment can be illustrated in Formula II below where r, s, t and v are as defined above.

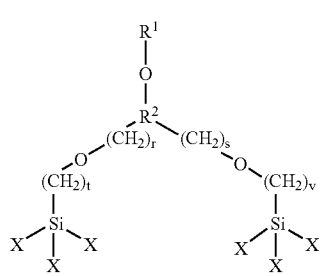
(II)

A further preferred embodiment according to Formula I includes a structure in which n is 2; y is 0 and $R^2$ is a straight chain alkoxy group having at least one C—O—C ether linkage. $R^3$ is an unsubstituted, straight chain alkyl group and $R^4$ is an unsubstituted, straight chain alkoxy group having at least one terminal ether linkage which bonds $R^4$ to $R^3$ and X is as defined above for Formula (II). This embodiment may be illustrated as below in Formula (III):

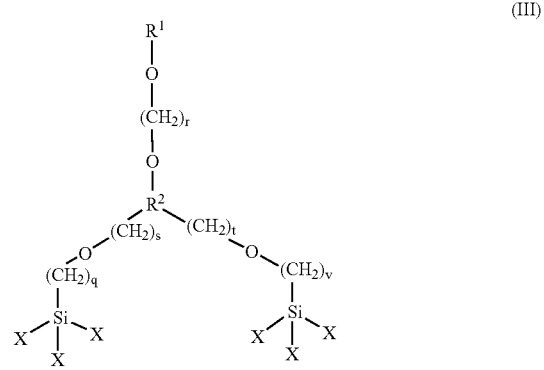
(III)

It the alternative embodiment of the above Formula (III), the podal branches may be modified to include more ether linkages within the alkyl groups linked to $R^2$ or in Formula (I) could encompass additional ether linkages in the podal branches in the bracketed groups above, with the exception of $R^3$.

Another preferred embodiment of Formula (I) in which n is 0; y is 2; $R^2$ is methyl; $R^3$ is an unsubstituted, straight chain, alkyl group and X is as noted above with respect to Formulae II-III. An example of such a structure is shown below in formula (IV):

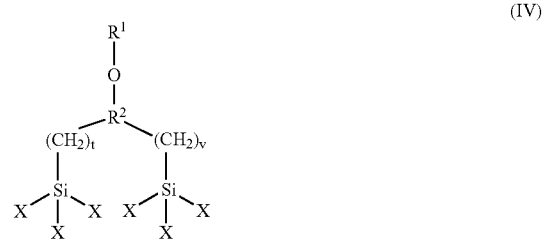
(IV)

An example of a result of the reaction of a polypodal silane, in the form of a preferred dipodal silane compound described herein with a substrate, preferably a siliceous substrate is the formation of six oxane bonds on two different centers, is depicted in Formula (V), below.

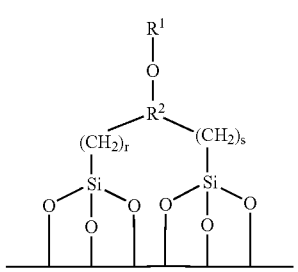
(V)

The above illustrates the contrast of the polypodal silanes of the invention with the structure of prior art silicon compounds previously used in bonded phases with only one point of attachment, as is shown directly below.

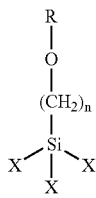

The practical consequence of the additional locations for bonding to the substrate are significant in environments where water is present and there is a continuous change in the mobile phase. Pleuddemann noted (Silane Coupling Agents, Plenum Press 1982, p. 127): "The bond between a silane-modified resin and a hydrophilic mineral surface is pictured as existing under equilibrium conditions of oxane bond formation and silanols in the presence of water." While few studies have been made on the equilibrium constant for the system:

the equilibrium constant is estimated to be $10^{(-2)}$ to $10^{(-3)}$. In order for a silane bonded phase to leave or be separated from the substrate surface after bonding, all bonds must be broken and appropriate conditions must be provided for the silane to diffuse from the substrate before bond formation can recur. For a silicon bonded phase with three oxane bonds the equilibrium constant for simultaneous hydrolysis of all bonds is $10^{-2(3)}$ to $10^{-3\,(3)}$. Practically, the loss of silane due to bleed is in the range of about 1% every three to ten days depending on conditions. If six oxane bonds are present, then the probability of retaining at least one oxane bond improves by a factor of $10^6$ to $10^9$, i.e., if the conventional silane loses 1% activity over five days, the dipodal silane of the invention would lose 1% over five million days.

The advantage of the polypodal, preferably dipodal bonded phases with embedded hydrophilicity of the invention described herein is that water and/or solvent molecules can have a continuous interaction with the bonded phase while allowing solute molecules to partition to the hydrophobic portion, i.e., a bonded hydrophobic phase is created with stable attachment to a solid substrate, but "connected" through an aqueous region, mitigating diffusional and bed collapse issues. Other possible applications for polypodal silanes described herein with embedded hydrophilicity include, but are not limited to solvent resistant coatings for varied uses such as as anti-graffiti coatings for siliceous architectural surfaces.

The invention further includes a method for preparing a bonded phase in which a polypodal silane compound is reacted with a chromatographic silica to form a bonded phase useful for separation or extraction. The polypodal silane compound is preferably that compound as described above in which the silane has at least two podal branches bonded by an ether linkage or alkoxy group to a hydrophilic group. Each podal branch has a silicon atom and each atom is bonded to each podal branch through a Si—C bond and each branch is capable of bonding to a siliceous substrate through at least one hydrolyzable functional group capable of being displaced by a Si—O bond.

The invention also encompasses within its scope a siliceous substrate bonded to a polypodal silane compound in which the polypodal silane compound has at least two podal branches bonded by an ether linkage or alkoxy group to a hydrophilic group. Each podal branch has a silicon atom, and the silicon atoms are bonded to each podal branch through a Si—C bond and each of the podal branches forms at least one Si—O—Si bond with the substrate. Preferably the substrate comprises silicon and is siliceous in nature, such as glass, a silicon wafer or other silicon coated surface.

This invention should also be differentiated from prior silanes having more than one silicon point of attachment to a substrate in which the silicon atoms have Si—O—Si bonds between each silicon or with the hydrophilic section. Due to the fact that the Si—O—Si bond is of the same nature as that which provided bonding to the substrate, it is subject to hydrolysis and renders the coupling to the substrate approximately equivalent to conventional silanes with only one point of attachment to the substrate.

Thus, the polypodal silicon compounds encompassed within the present description which have two or more silicon atoms linked to the remainder of the bonded phase by Si—C bonds then bond to the substrate by at least one non-hydrolyzable functional group on each silicon that is enables the structure to be capable of bonding at multiple points to the substrate and still retains a polar substituent capable of hydrogen-bonding with water.

The compounds of the invention may be prepared by any acceptable synthesis know or to be developed in the art. As an example, the most readily available starting materials are glycerol (1,2,3-trihydroxypropane), 1,1,1-trimethylolpropane, trimethylolethane, and 1,5-dihydroxy-3-hydromethylpentane. While there are a variety of synthetic methods possible to achieve the desired products, the preferred synthesis includes preparing di-unsaturated ethers from alcohols, followed by hydrosilylation. If a free hydroxyl group remains in the final product then, in order to prepare more discrete and easily characterized compounds, it is useful to protect the free hydroxyl group prior to hydrosilylation and deblock after hydrosilylation. For example, the diallylether of glycerol can be hydrosilylated directly, or the trimethylsilylether of the free hydroxyl group can be prepared, the hydrosilylation effected, and the trimethylsilyl group removed. Polypodal silanes can also be produced from starting materials such as pentaerythritol triallyl ether.

The invention will be further illustrated below in the following non-limiting examples:

EXAMPLE 1

2,2-Bis(allyloxymethyl)-1-trimethylsiloxybutane having the structure shown below

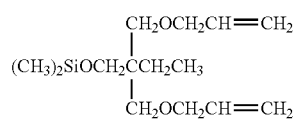

was prepared by the trimethylsilylation of trimethylolpropane diallyl ether with hexamethyldisilazane followed by fractional distillation. The resulting compound had the following properties: purity 95%; observed b.p. 140-144° C./25 mm; density 0.892; refractive index: 1.4367 and $^1$HNMR ($C_6D_6$): 0.12(s, 9H), 0.98(t, 3h), 1.62(q, 2H), 3.37(s, 4H), 3.67(m, 2H), 3.81 (m, 2H), 5.05(m, 2H), 5.25(d, 2H), 5.89(m, 2H).

EXAMPLE 2

2,2-Bis(3-triethoxysilylpropoxymethyl)-1-trimethylsiloxybutane

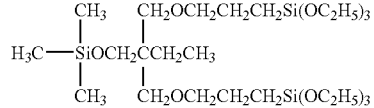

A 1-liter, 3-neck flask equipped with magnetic stirrer, pot thermometer, addition funnel and condenser was charged with 143.2 g of 2,2-Bis(allyloxymethyl)-1-trimethylsiloxybutane. After heating to ~80° C., 35 g of triethoxysilane was added followed by 1 ml of Karstedt catalyst containing 2% Pt. Once initiation was observed, the balance of triethoxysilane (133.4 g) was added at a rate to maintain temperature at 80-110° C. When the addition was complete, an additional 0.5 ml of Karstedt catalyst was added and temperature of 90° C. was maintained for 2 hours. A GC indicated the reaction was not complete. Two additional portions 43 g of triethoxysilane and 0.5 g of Karstedt were added, maintaining the temperature at 95-105° C. The product was purified by means of a wiped-film evaporator, removing volatiles on a first pass and then distilling crude product on a second pass. A short-path distillation produced purified product: b.p.: 200-205° C. at 0.8 mm; density: 0.980; $^1$HNMR($C_6D_6$): 0.13(s, 9H), 0.77(m, 4H), 1.00(m, 3H), 1.14(t, 18H), 1.18(m, 2H), 1.85(m, 4H) 3.38(dd, 8H), 3.76(s, 2H), 3.81(q, 12H). The FTIR showed a strong absorption at 1105.1 $cm^{-1}$, which is characteristic of Si—O.

EXAMPLE 3

2,2-Bis(3-triethoxysilylpropoxymethyl)butanol 50% in EtOH

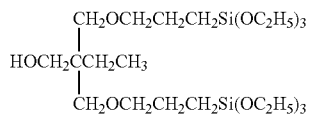

A 200 ml 3-neck flask equipped with magnetic stirrer, pot thermometer and condenser was charged with 2,2-bis(3-triethoxysilylpropoxymethyl)-1-trimethylsiloxybutane (46.1 g), excess ethanol and acetic acid (0.5 g). The mixture was refluxed for two hours and concentrated to 50% active solids, removing trimethylethoxysilane and excess ethanol. The product had a density of 0.8988; $^1$HNMR ($C_6D_6$): 0.70(m, 4H), 0.84(m, 3H), 1.12(m, 18H), 1.16(m, 2H), 1.74(m, 4H), 3.36(dd, 8H), 3.53(q, 12H), 3.74(s, 2H). The FTIR showed a strong absorption at 1104 $cm^{-1}$, which is characteristic of Si—O.

EXAMPLE 4

3,3-Diallyloxymethyl-5-oxa-tridecane

A 5 L, 4-neck flask equipped with magnetic stirrer, pot thermometer and condenser was charged with 1 L of toluene, 214.3 g (1 M) of trimethylolpropanediallylether and 23.0 g of sodium metal. The mixture was heated to 110-110° C. for approximately 4 hours during which time the sodium was slowly consumed. Bromooctane (241.4 g) was added rapidly. The mixture was heated to reflux for 6-10 hours, during which time a white precipitate formed. The mixture was allowed to return to room temperature and 0.5 L of water was added. The organic layer was separated, washed with an additional 0.5 L of water, dried over sodium sulfate and then distilled. Isolated yield of the product was 178 g (55%), b.p. 134-6° C./0.3 mm; density: 0.937; $^1$HNMR ($C_6D_6$): 0.84 (m, 5H), 1.11(m, 10), 1.40(m, 5H), 2.97 (t, 2H), 3.35(m, 4H), 3.76(dd, 4H), 5.01(dd, 2H), 5.22(dd, 2H), 5.75(m, 2H).

EXAMPLE 5

3,3-Bis(trichlorosilylpropoxymethyl)-5-oxa-tridecane

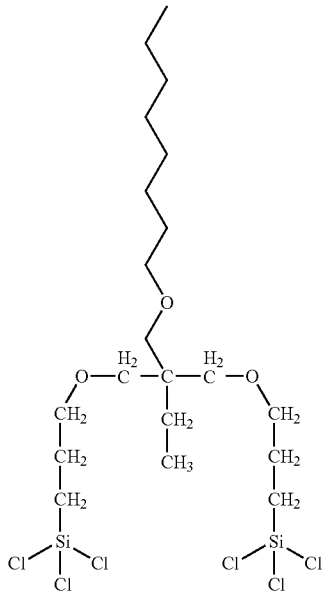

A 1 L, 3-neck flask equipped with magnetic stirrer, pot thermometer and condenser was charged with 3,3-diallyloxymethyl-5-oxa-tridecane (200 g) prepared in Example 4. After heating to 50-60° C., 30 ml of trichlorosilane was added followed by 1 ml of 2.5% chloroplatinic acid solution. Once initiation was observed, a total of 178.8 g of trichlorosilane was added at a rate to maintain reaction temperature at 70-100° C. After the addition was complete, the mixture was maintained at 80-90° C. for 2 hours. The mixture was distilled. The product was isolated in 60% yield, b.p. 220-222 C./0.9 mm; density 1.135; $^1$HNMR ($C_6D_6$): 0.90(m, 6H), 1.13(m, 4H), 1.26(m, 10H), 1.58(m, 8H), 3.10(t, 4H), 3.32(s, 2H), 3.38(t, 4H).

EXAMPLE 6

1,3-Bis(3-trichlorosilylpropoxy)-2-decyloxypropane

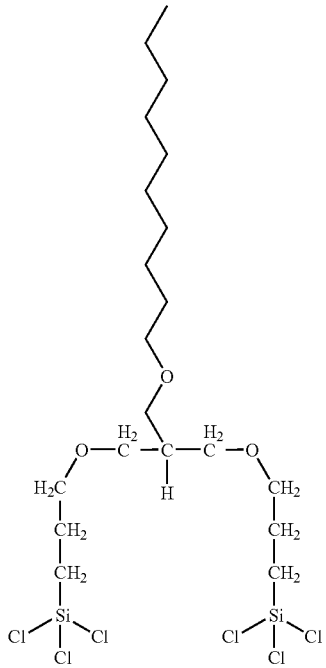

A 2 L, 4-neck flask equipped with magnetic stirrer, pot thermometer and condenser was charged with 500 ml of toluene, 172.2 g (1 M) of glycerol diallylether and 23.0 g of sodium metal. The mixture was heated to 110-110° C. for approximately 4 hours during which time the sodium was slowly consumed. Bromodecane (232.25 g) was added rapidly. The mixture was heated to reflux for 6-10 hours, during which time a white precipitate formed. The mixture was allowed to return to room temperature and 0.5 L of water was added. The organic layer was separated, washed with an additional 0.5 L of water, and dried over sodium sulfate. The volatile components were removed by distillation. As in Example 5, trichlorosilane was added in the presence of a Pt catalyst. The product was distilled at 180-200° C. at 0.4 mmHg. The gas chromatograph (GC) indicated a purity of 93.4% with one close peak, presumably the isomeric 2 trichlorosilyl addition product.; $d^{20}=1.576$; $^1$HNMR (CDCl$_3$): 0.91(t, 3H), 1.31(m, 14H), 1.47(m, 4H), 1.82(m, 3H), 3.56(m, 10H).

Based on the above examples, it should be understood according to this disclosure that a bonded phase can be prepared by reacting the silanes of this invention with chromatographic silica to form bonded phases for separation. A substrate can be modified for DNA, RNA, nucleic acid, peptide, antibody, or protein attachment by bonding silanes of this invention where $R^1$ is a hydrogen atom.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A polypodal silane compound for use as a bonded phase and having hydrophilicity, comprising at least two podal branches bonded via an ether linkage or alkoxy group to a hydrophilic group, wherein each podal branch has a silicon atom, the silicon atoms are bonded to each podal branch through a Si—C bond and each of the podal branches is capable of bonding to a siliceous substrate through at least one hydrolyzable functional group capable of being displaced by a Si—O bond, and wherein the compound has a structure according to Formula (I):

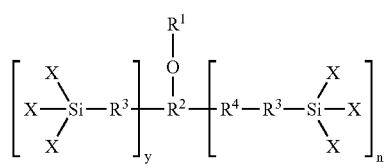

wherein:
$R^1$ is selected from hydrogen, and substituted and unsubstituted, branched and straight chain, alkyl, alkenyl, alkynyl, aryl, alkylene ether, alkenyl ether, alkynyl ether or aryl ether groups, and wherein, in $R^1$, oxygen atoms are not bonded together so as to form peroxy functionality;
$R^2$ is selected from substituted and unsubstituted, branched and straight chain alkyl and alkylene ether groups;
$R^3$ is selected from substituted and unsubstituted, branched and straight chain alkyl groups, wherein each $R^3$ group in Formula (I) may be the same or different;
$R^4$ is selected from substituted and unsubstituted, branched and straight chain alkyl, alkylene, alkylene ether and alkenyl ether groups, and an ether linkage;
X is a hydrolyzable group capable of bonding to a siliceous substrate and of being displaced by a silicon-oxygen bond or a non-hydrolyzable organic functional group, wherein at least one of the X groups on each Si atom is hydrolyzable;
n is 0 or an integer which is no greater than 3;
y is 0 or an integer which is no greater than 3; and
wherein $2 \leq n+y \leq 3$; and n and y are never both zero.

2. A polypodal silane compound comprising a structure according to Formula (I):

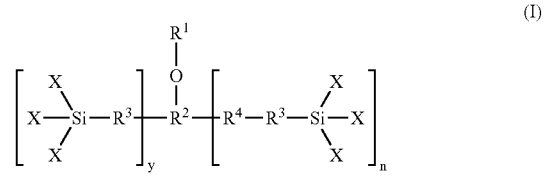

wherein:
$R^1$ is selected from hydrogen, and substituted and unsubstituted, branched and straight chain, alkyl, alkenyl, alkynyl, aryl, alkylene ether, alkenyl ether, alkynyl ether or aryl ether groups, and wherein, in $R^1$, oxygen atoms are not bonded together so as to form peroxy functionality;
$R^2$ is selected from substituted and unsubstituted, branched and straight chain alkyl and alkylene ether groups;
$R^3$ is selected from substituted and unsubstituted, branched and straight chain alkyl groups, wherein each $R^3$ group in Formula (I) may be the same or different;
$R^4$ is selected from substituted and unsubstituted, branched and straight chain alkyl, alkylene, alkylene ether and alkenyl ether groups, and an ether linkage;
X is a hydrolyzable group capable of bonding to a siliceous substrate and of being displaced by a silicon-oxygen bond or a non-hydrolyzable organic functional group, wherein at least one of the X groups on each Si atom is hydrolyzable;
n is 0 or an integer which is no greater than 3;
y is 0 or an integer which is no greater than 3; and
wherein $2 \leq n+y \leq 3$; and n and y are never both zero.

3. The polypodal silane compound according to claim 2, wherein X is selected from an alkoxy group, a halogen, a carboxylate, and a non-hydrolyzable organic functional group.

4. The polypodal silane compound according to claim 2, wherein $R^1$ is selected from substituted and unsubstituted, branched or straight chain alkyl or alkylene ether groups of from 1 to 30 carbons.

5. The polypodal silane compound according to claim 2, wherein $R^1$ is capable of interacting, binding or covalently linking to a the biological polymer selected from the group consisting of peptides, polypeptides, oligonucleotides, and proteins bonded to the oxygen attached to $R^1$ in Formula (I) by an ester or amide linkage.

6. The polypodal silane compound according to claim 2, wherein each of the X groups, is hydrolyzable.

7. The polypodal silane compound according to claim 2, wherein n is 0; y is 2; $R^2$ is methyl; $R^3$ is selected from unsubstituted, straight chain alkyl groups of from 1 to 10 carbon atoms; and X is selected from the group consisting of methoxy, ethoxy, chlorine, acetate, methyl, and isopropyl.

8. The polypodal silane compound according to claim 7, wherein $R^3$ has from 3 to 5 carbon atoms.

9. The polypodal silane compound according to claim 2, wherein n is 2; y is 0; $R^2$ is methyl; $R^3$ is selected from unsubstituted, straight chain alkyl group of from 1 to 10 carbon atoms; $R^4$ is selected from unsubstituted, straight chain alkylene ethers of from 1 to 10 carbon atoms having a least one terminal ether linkage which bonds $R^4$ to $R^3$; and X is selected from the group consisting of methoxy, ethoxy, chlorine, acetate, methyl and isopropyl.

10. The polypodal silane compound according to claim 2, wherein n is 2; y is 0; $R^2$ is a straight chain alkylene ether group of from 1 to 10 carbon atoms having at least one C—O—C ether linkage; $R^3$ is selected from unsubstituted, straight chain alkyl groups of from 1 to 10 carbon atoms; $R^4$ is selected from unsubstituted, straight chain alkylene ether groups of form 1 to 10 carbon atoms having at least one terminal ether linkage which bonds $R^4$ to $R^3$; and X is selected from the group consisting of methoxy, ethoxy, chlorine, acetate, methyl and isopropyl.

11. The polypodal silane compound according to claim 2, wherein at least one of the podal branches bracketed in Formula (I) has two or more ether linkages.

* * * * *